US008979869B2

(12) United States Patent
Starr

(10) Patent No.: US 8,979,869 B2
(45) Date of Patent: Mar. 17, 2015

(54) CIRCUMCISION SCISSOR

(71) Applicant: LaVoyce Starr, Inglewood, CA (US)

(72) Inventor: LaVoyce Starr, Inglewood, CA (US)

( * ) Notice: Subject to any disclaimer, the term of this patent is extended or adjusted under 35 U.S.C. 154(b) by 204 days.

(21) Appl. No.: 13/627,976

(22) Filed: Sep. 26, 2012

(65) Prior Publication Data

US 2013/0079795 A1 Mar. 28, 2013

Related U.S. Application Data

(60) Provisional application No. 61/626,438, filed on Sep. 26, 2011.

(51) Int. Cl.
*A61B 17/32* (2006.01)
*A61B 17/326* (2006.01)

(52) U.S. Cl.
CPC ............................ *A61B 17/326* (2013.01)
USPC ........................................................ 606/118

(58) Field of Classification Search
CPC .. A61B 17/326; A61B 17/285; A61B 17/295; A61B 2017/320072; A61B 2017/32113
USPC ......... 606/118, 167, 168, 170, 172, 174, 175; 30/134, 135
See application file for complete search history.

(56) References Cited

U.S. PATENT DOCUMENTS

| 1,765,319 | A | * | 6/1930 | Williams ...................... 606/118 |
| 2,471,864 | A | * | 5/1949 | De Palo ........................ 606/118 |
| 2,548,670 | A | * | 4/1951 | Hyatt ............................ 606/118 |
| 2,553,697 | A | * | 5/1951 | Zacrep ............................ 30/135 |
| 2,601,470 | A | * | 6/1952 | Turner .......................... 606/118 |
| 2,686,521 | A | * | 8/1954 | Sheldon et al. ............... 606/118 |
| 5,250,056 | A | * | 10/1993 | Hasson ......................... 606/151 |
| 6,767,349 | B2 | * | 7/2004 | Ouchi ............................. 606/51 |
| 7,871,423 | B2 | * | 1/2011 | Livneh ......................... 606/205 |
| 2006/0122626 | A1 | * | 6/2006 | Duel ............................. 606/118 |
| 2007/0191713 | A1 | * | 8/2007 | Eichmann et al. ............ 600/471 |
| 2008/0021482 | A1 | * | 1/2008 | Tomlinson .................... 606/118 |
| 2010/0121367 | A1 | * | 5/2010 | Lin et al. ...................... 606/174 |

* cited by examiner

*Primary Examiner* — Tuan V Nguyen
*Assistant Examiner* — Chima Igboko
(74) *Attorney, Agent, or Firm* — John K. Buche; Buche & Associates, P.C.

(57) ABSTRACT

A circumcision scissor for performing a circumcision is described herein. The circumcision scissor has a grip system similar to that of cutting scissors. A knob operates a plurality of legs to move a blade housing. The blade housing contains a circular blade configured to sever foreskin for removal from a penis. The penis is held secure in a clear tube to prevent injury to the penile gland.

7 Claims, 3 Drawing Sheets

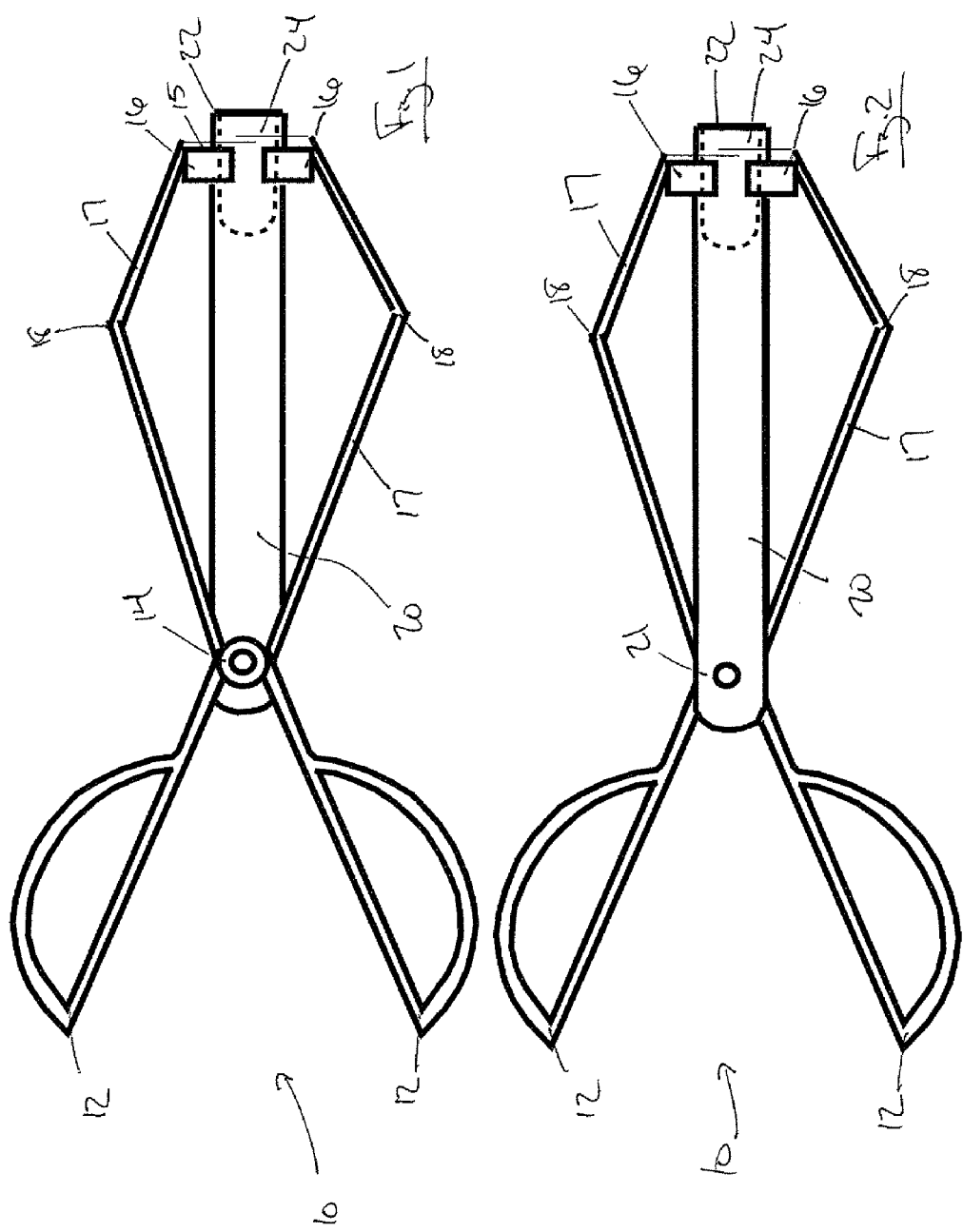

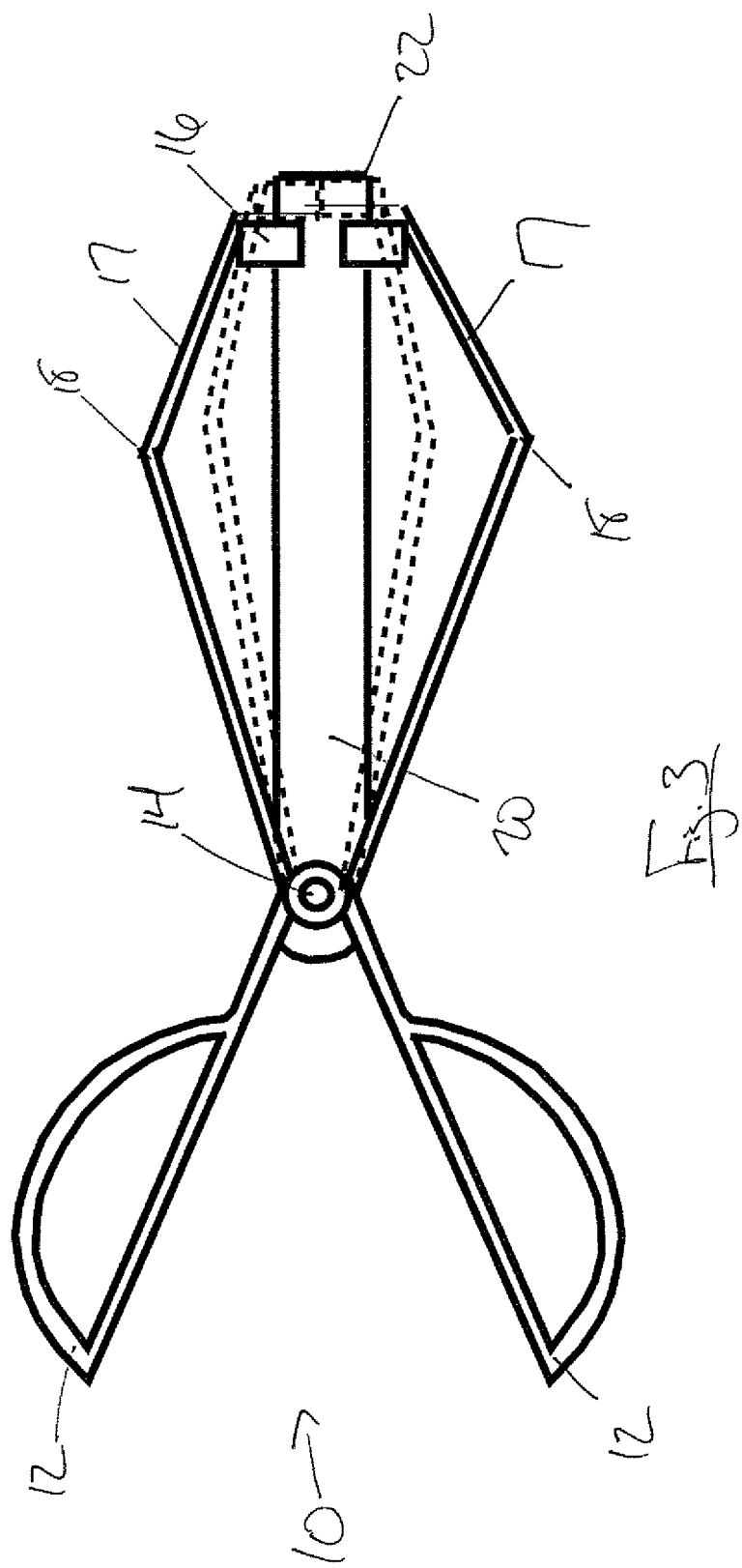

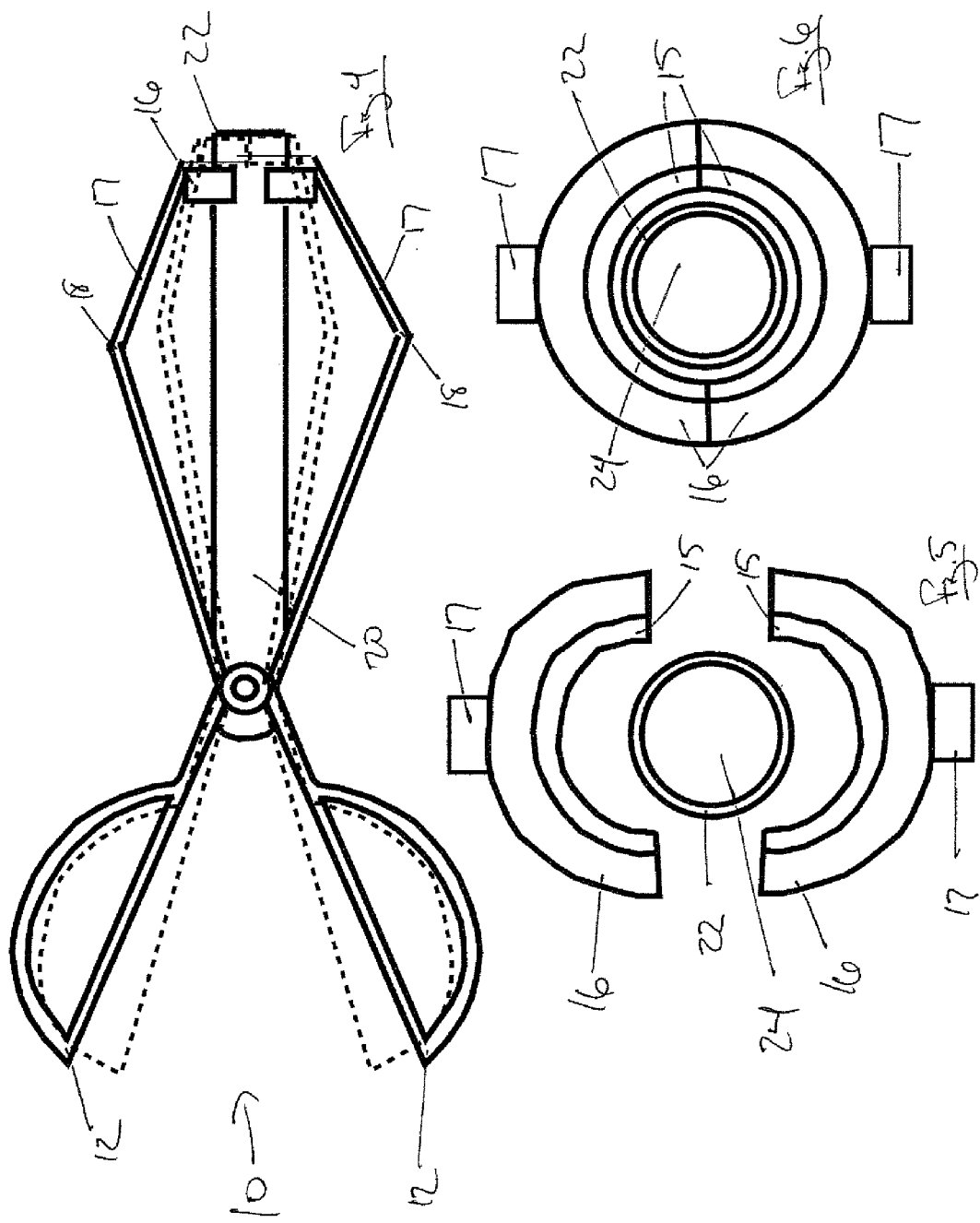

CIRCUMCISION SCISSOR

PRIORITY CLAIM

This application claims the benefit of priority to U.S. Provisional Pat. App. Ser. No. 61/626,438, filed Sep. 26, 2011. The disclosure of which is hereby incorporated in its entirety by this reference.

FIELD OF THE INVENTION

The present invention generally relates to surgical devices and methods. More specifically, the present invention relates to surgical devices for performing circumcisions.

BACKGROUND OF THE INVENTION

Circumcision is the act of surgically removing foreskin from a penis. The procedure is commonly performed for medical and/or religious purposes. Some surveys find that approximately 56% of newborn boys undergo circumcision in hospitals. Surgical scissors may be used to perform the procedure. Dedicated circumcision apparatuses are well known in the art as well. Such apparatuses include, but are not limited to, the Mogen clamp and the Gomco clamp.

The Mogen clamp was described in U.S. Pat. No. 2,747,576 to Bronstein. The Mogen clamp was once one of the more preferred methods for performing a circumcision. However, the procedure based around the Mogen clamp has recently been criticized as being dangerous as it can lead to severe, irreversible injuries. Two manufacturers of the Mogen clamp were subject to multimillion dollar lawsuits as a result of partial amputation of the penis. Since then, those two manufacturers have ceased distribution of the Mogen clamps.

One design of the Gomco clamp was described in U.S. Pat. No. D119,180 to Goldstein. The Gomco clamp requires use of a scalpel when performing to the circumcision. There is also a risk of cutting the urethra when performing the procedure in preparation of use of the clamp.

Consequently, there is a need in the art for a new and improved circumcision apparatus and method. It is an object of the present invention to provide a safer apparatus and method of circumcision by providing more visibility of the penis during the procedure. It is another object of the present invention to provide a cutting system and method to create an incision in a faster and safer manner.

SUMMARY OF THE INVENTION

The present invention is directed to an apparatus for performing a circumcision on a penis. A circumcision scissor is disclosed herein having a blade housing made up of a plurality of blade housing portions. A circular blade is embedded in the blade housing. A user may grip the circumcision scissor by a plurality of eye ring grips. The circumcision scissor further has a plurality of legs with a leg joint along a middle portion of each of the plurality of legs. The leg joints may be straightened to extend the plurality of legs by rotating a knob to activate a connecting wire between the knob and the blade housing running along the plurality of legs. The knob is positioned at a meeting point of the plurality of eye ring grips and the plurality of legs.

A tube, having an anchor end, an inner cavity and an open end, runs from the knob to the circular blade. The anchor end of the tube is attached opposite of the knob. The open end is configured to receive a penile gland of a penis. The inner cavity of the tube may also have an adhesive to secure and prevent movement of the penile gland. The blade housing and the tube are constructed from a clear material, such as polycarbonate plastic, to allow an unobstructed view of the penis to ensure an accurate circumcision.

The present invention is also directed to a method of circumcision with the steps of inserting a penile gland of a penis into a tube, rotating a knob to extend the plurality of legs into a desired position, clamping the penis with the circular blade and creating an incision on a foreskin of the penis. The knob may be connected to the circular blade by a connecting wire running along the plurality of legs.

The circular blade may be embedded in a blade housing to provide for structural stability. The blade housing and the tube may be constructed from a clear material, such as polycarbonate plastic, to allow for an unobstructed view of the penis to verify proper positioning of the penis. The inner cavity of the tube may also have an adhesive to secure the penile gland.

The present invention is further directed to an apparatus for circumcising a penis having a blade housing, a circular blade, a plurality of eye ring grips, a plurality of legs, and a tube. The apparatus is configured to be operated similar to the above circumcision scissor by using the plurality of eye ring grips as the operable mechanical force as opposed to the knob. The circular blade is configured within the blade housing. The plurality of eye ring grips are hingedly coupled to the plurality of legs.

The tube is configured to protect the penile gland from severe injury by having an anchor end, an inner cavity and an open end. The tube runs from a midpoint intersection of the plurality of eye ring grips and the plurality of legs. The open end is configured to receive a penile gland of a penis.

While the apparatus has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a side view of a circumcision scissor;

FIG. 2 is an opposite side view of the circumcision scissor;

FIG. 3 is a side view of the circumcision scissor in a first state of operation, wherein a second state of operation is illustrated in dotted lines;

FIG. 4 is a side view of an alternative embodiment of the circumcision scissor in a first state of operation, wherein a second state of operation is illustrated in dotted lines;

FIG. 5 is a front view of the circumcision scissor in a first state of operation highlighting an open end of a tube, a blade housing made up of blade housing portions, and a circular blade; and FIG. 6 is a front view of the circumcision scissor in a second state of operation.

DETAILED DESCRIPTION OF THE PREFERRED EMBODIMENTS

With reference to the drawings, FIGS. 1 and 2 are opposite side views of a circumcision scissor 10 configured to circumcise a penis and removing foreskin from the penis. The circumcision scissor 10 may be held by a user with a plurality of eye hole grips 12. In a preferred embodiment, the plurality of eye hole grips 12 have a rounded surface on an outer aspect and a straight surface on an inner aspect. The plurality of eye hole grips 12 may alternatively be of any geometric shape, such as square, circular or rectangular without departing from the scope of the present invention. The circumcision scissor has a midpoint which is the preferred position of a knob 14. The knob 14 is configured to extend or contract a plurality of legs 17. The plurality of legs 17 each have a leg joint 18 to facilitate movement controlled by the knob 14. The knob 14 may operate the plurality of legs 17 by any suitable method of mechanical construct such as by gears or a connecting wire.

At a base end of the plurality of legs 17, there is a blade housing 16 configured to separate into a plurality of blade housing portions, each of which is coupled to each of the plurality of legs 17. A circular blade 15 is embedded within the blade housing 16, wherein the circular blade 15 is configured to make an incision in the foreskin. The blade housing 16 is preferably constructed from a clear polycarbonate plastic to allow the user to properly see where the penis is located relative to the circumcision scissor 10. Other materials may be used without departing from the scope of the present invention.

The circumcision scissor 10 has a tube 20 preferably configured to extend from the midpoint and the knob 14 to the base end of the plurality of legs 17. This preferred construction allows for stability when performing the circumcision. The tube 20 has an anchor end 21, an inner cavity 24 and an open end 22. The open end 22 is configured to allow the penile gland to enter the inner cavity 24. The inner cavity 24 may have adhesive to secure and prevent movement of the penile gland during the procedure. The tube 20 is preferably constructed from a clear polycarbonate plastic to allow the user to properly see where the penis is located relative to the circumcision scissor 10. Other materials may be used without departing from the scope of the present invention.

With regard to FIG. 3, two states of use of the circumcision scissor 10 are illustrated. A neutral state is shown in solid lines, and an operative state is shown in dotted lines. The knob 14 is turned to straighten out the plurality of legs 17 at the leg joints 18. By straightening the plurality of legs 17, the blade housing 16 is pushed together to couple the blade housing portions. When the blade housing 16 is complete, the circular blade 15 comes together to clamp onto the penis and to sever the foreskin. The resulting incision begins the process of circumcision. Turning the knob 14 further causes the circular blade 15 to move in a circular motion to fully create an incision around the foreskin. Thus, the foreskin may be removed from the penis. FIG. 4 illustrates an alternative embodiment in which the knob 14 is not used to operate the plurality of legs 17. The plurality of eye hole grips 12 would operate the plurality of legs 17 in a manner similar to that of cutting scissors or hemostats.

FIGS. 5 and 6 illustrate a front view of the circumcision scissor 10. FIG. 5 illustrates a neutral state in which the blade housing 16 is recessed away from the open end 22 and the inner cavity 24 of the tube 20. FIG. 6 illustrates the circumcision scissor 10 after the knob 14 is turned to operate the plurality of legs 17. The blade housing 16 and circular blade 15 preferably form circles after coupling each respective half.

The tube 20 has the penile gland within the inner cavity 24 during the circumcision, so the penile gland is protected from severe but accidental injury. The blade housing 16 is preferably configured in a way to create only a deep enough incision to remove the foreskin and to not create a deeper cut into the penis.

While circumcisions are generally performed on neonates, circumcisions may also be performed on children or adults. Accordingly, the circumcision scissor 10 may be constructed in different sizes without departing from the scope of the invention. The circumcision scissor 10 is also preferably constructed substantially of plastic to allow for disposability. By making the circumcision scissor 10 disposable, costs can be kept low per instrument while also obviating the need for sterilization of the circumcision scissor 10 between uses.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

While the particular Circumcision Scissor as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for circumcision, comprising the steps of:
    inserting a penile gland of a penis into a tube, wherein the tube is coupled to a plurality of legs;
    rotating a knob to extend the plurality of legs into a desired position;
    clamping the penis with a circular blade; and
    creating an incision on a foreskin of the penis;
    wherein the knob further comprises a connecting wire to connect the knob to the circular blade.

2. The method for circumcision of claim 1, further comprising the step of looking through the tube to verify proper positioning of the penis, wherein the tube is constructed from a clear polycarbonate plastic to allow for an unobstructed view within the tube.

3. The method for circumcision of claim 1, wherein the circular blade is embedded in a blade housing.

4. The method for circumcision of claim 3, wherein the blade housing is constructed from a clear polycarbonate plastic to allow for an unobstructed view through the blade housing.

5. The method for circumcision of claim 1, further comprising the step of adhering the penis to an inner cavity of the tube to prevent movement within the tube.

6. A method for circumcision, comprising the steps of:
   inserting a penile gland of a penis into a tube, wherein the tub is coupled to a plurality of legs;
   rotating a knob to extend the plurality of legs into a desired position;
   clamping the penis with a circular blade
   creating an incision on a foreskin of the penis; and
   rotating the circular blade with the knob to sever the foreskin for removal from the penis.

7. A method of circumcision of claim 1 wherein the movement of the circular blade is controlled by eye hole grips.

* * * * *